United States Patent
Hanson et al.

(10) Patent No.: US 7,114,143 B2
(45) Date of Patent: Sep. 26, 2006

(54) PROCESS YIELD LEARNING

(75) Inventors: Jeffrey F. Hanson, Portland, OR (US); Ryan C. Fredrickson, Portland, OR (US)

(73) Assignee: LSI Logic Corporation, Milpitas, CA (US)

( * ) Notice: Subject to any disclaimer, the term of this patent is extended or adjusted under 35 U.S.C. 154(b) by 210 days.

(21) Appl. No.: 10/696,203

(22) Filed: Oct. 29, 2003

(65) Prior Publication Data

US 2005/0097482 A1  May 5, 2005

(51) Int. Cl.
*G06F 17/50* (2006.01)
(52) U.S. Cl. .............. 716/19; 716/1; 716/2; 716/4; 716/21
(58) Field of Classification Search ............ 716/1, 716/2, 19, 21, 4
See application file for complete search history.

(56) References Cited

U.S. PATENT DOCUMENTS

| | | | |
|---|---|---|---|
| 5,128,737 A * | 7/1992 | van der Have | 257/503 |
| 5,475,695 A * | 12/1995 | Caywood et al. | 714/738 |
| 6,185,707 B1 * | 2/2001 | Smith et al. | 714/724 |
| 6,542,830 B1 * | 4/2003 | Nakazato et al. | 702/35 |
| 6,553,329 B1 * | 4/2003 | Balachandran | 702/118 |
| 6,701,477 B1 * | 3/2004 | Segal | 714/732 |
| 6,707,936 B1 * | 3/2004 | Winter et al. | 382/149 |
| 2005/0066294 A1 * | 3/2005 | Templeton et al. | 716/1 |

OTHER PUBLICATIONS

Bichebois et al.,"Analysis of Defect to Yield Correlation of Memories: Method, Algorithms and Limits", Oct. 1997 IEEE International Symposium on Defect and Fault Tolerance in VLSI Systems, Proceedings pp. 44-52.*
Cheema et al.,"Wafer Back Side Inspection Applications for Yield Protection and Enhancement", May 2002, IEEE/SEMI Advanced Semiconductor Manufacturing Conference, Paper Digest pp. 64-71.*

* cited by examiner

Primary Examiner—Sun James Lin
(74) Attorney, Agent, or Firm—Luedeka, Neely & Graham

(57) ABSTRACT

A method for producing yield enhancement data from integrated circuits on a substrate. A database of defects on the substrate is compared to a database of design information for the integrated circuits. The defects on the substrate are associated with classes of design information to produce the yield enhancement data.

15 Claims, 1 Drawing Sheet

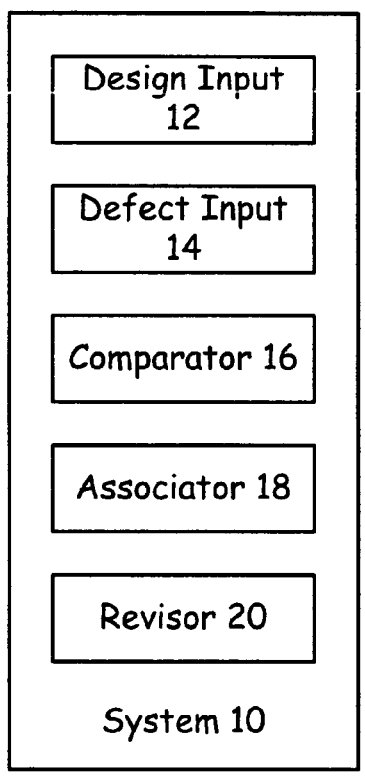

Design Input 12

Defect Input 14

Comparator 16

Associator 18

Revisor 20

System 10

PROCESS YIELD LEARNING

FIELD

This invention relates to the field of integrated circuit fabrication. More particularly, this invention relates to defect analysis of integrated circuits.

BACKGROUND

Integrated circuits have developed into enormously complex structures. Not only are there millions of devices in a state of the art integrated circuit, but the number of such devices tends to double every eighteen months or so. In addition to having a greater number of devices, integrated circuits are being fabricated with devices that are continually reduced in size, and disposed at ever decreasing distances one from another. Thus, integrated circuits are becoming smaller and more complex, all at the same time.

Because there are more and smaller devices within each integrated circuit, a physical defect on the substrate, such as may be caused by contamination or a processing flaw, tends to be very detrimental to the proper operation of the integrated circuit. One reason for this is that any defect on the substrate tends to impact the proper formation of one or more of the devices within the integrated circuit, since there are so many devices, and the devices are placed so close to one another. By way of comparison, in the past, when devices were generally larger and placed farther apart, there was more room on the substrate where a defect could occur, and which did not touch any of the devices of the integrated circuit, or perhaps was not the type of defect which would damage the few devices that it did touch. This situation no longer exists.

Thus, there is a great deal of attention paid to ensuring that the processes and materials that are used in integrated circuit fabrication do not contain or create defects on the substrate. For example, integrated circuits are typically formed on substrates that include a semiconducting portion, such as Group IV materials like silicon and germanium, or Group III-V compounds such as gallium arsenide, or composites of such materials. Much attention is given to ensure that these substrates are defect free at the on-set of processing, so that there are no known defects that would decrease the expected yield of the integrated circuits at the end of the fabrication process.

Similar precautions are taken with the other materials that are used during the fabrication process. For example, all of the gasses, liquids, metals, dielectrics, and organics that are used during the fabrication process are refined to an extremely pure state, so that they do not introduce materials that might behave in a unknown or undesirable manner during processing, or otherwise introduce defects, such as by contaminating the substrate.

Further, the processes that are used to fabricate the integrated circuits are inspected and controlled to a high degree, typically using techniques such as statistical process control, to ensure that the processes themselves do not create defects within the integrated circuits. For example, certain processes are closely watched to ensure that they do not create flakes or chips that might deposit onto the surface of the substrate, and thereby create defects in the integrated circuits. Process reaction chambers are periodically cleaned to prevent such flaking and other forms of contamination, so that the processing itself does not create defects.

Defect information, such as is determined by inspections during the fabrication process, is also correlated with electrical or other functional failures of integrated circuits, both at the testing down at the end of the substrate level fabrication process, generally known as wafer sort, and also after the individual integrated circuits are packaged, generally known as final test. Such correlations can be extended to a determination of whether the failure of the integrated circuit was due to a processing problem or a materials problem.

However, even though there is good correlation between processing problems and defects, and between materials problems and defects, and between defects and electrical failures, more information in regard to the correlation and correction of defect issues is needed. There is a need, therefore, for a system whereby defects are correlated with integrated circuit designs, such as the structures that are formed during integrated circuit fabrication.

SUMMARY

The above and other needs are met by a method for producing yield enhancement data from integrated circuits on a substrate. A database of defects on the substrate is compared to a database of design information for the integrated circuits. The defects on the substrate are associated with classes of design information to produce the yield enhancement data.

In this manner, the defect data for the substrate is associated with the design information for the integrated circuits. By so doing, a correlation of defects with classes of design information can be produced, which can be used to enhance integrated circuit yields. For example, by correlating defects with different classes of design information, it can be determined whether any of the various classes are more susceptible to defects than the others of the classes, or what classes are more susceptible to which defects. Thus, the defect data has in this embodiment been correlated with the actual design of the integrated circuits, rather than with the materials of which they are formed, or the processes by which they are formed. In this regard, the defect information is providing yield enhancement data of a type that has not previously been generated or considered.

In various embodiments, the database of defects is a defect wafer map. Preferably, the defects on the substrate are optically observable defects. The design information preferably includes structures formed in the integrated circuits. Preferably, the classes of design information include classes of physical structures. The database of defects is preferably created by inspections of the substrate, where the inspections are conducted at multiple times during fabrication of the integrated circuits. Preferably, the database of design information is created from design files for the integrated circuits. The design information is preferably revised based at least in part on the yield enhancement data.

According to another aspect of the invention there is described a method for producing yield enhancement data from integrated circuits on a substrate. A database of design information for the integrated circuits is created, where the design information is used as a template for fabricating the integrated circuits. A database of defects on the substrate is created during processing of the integrated circuits, and the database of design information is compared with the database of defects to create associations between the design information and the defects. The database of defects is associated with the database of design information by physical proximity of the defects to classes of the design information to produce the yield enhancement data.

In various embodiments of this aspect of the invention, the database of defects includes a defect wafer map. The defects on the substrate are preferably optically observable defects. The design information preferably includes structures formed in the integrated circuits. Preferably, the classes of design information include classes of physical structures. The step of creating the database of defects preferably includes inspections of the substrate, where the inspections are conducted at multiple times during the fabrication of the integrated circuits. Preferably, the design information is revised based at least in part on the yield enhancement data.

According to yet another aspect of the invention there is described a computerized system for analyzing defects, including means for receiving design information for integrated circuits, where the integrated circuits are fabricated on a substrate based on the design information. Means for receiving defect information for integrated circuits are also included, where the defect information contains locations of defects on the substrate. The system also includes means for comparing the design information with the defect information. Means are also used for associating the defects with classes of the design information based on physical proximity on the substrate to produce yield enhancement data.

In various embodiments, the defect information is a defect wafer map. Preferably, means are also included for revising the design information based at least in part on the yield enhancement data. Preferably, the design information includes structures formed in the integrated circuits. The classes of the design information preferably include classes of structures formed in the integrated circuits.

BRIEF DESCRIPTION OF THE DRAWINGS

Further advantages of the invention are apparent by reference to the detailed description when considered in conjunction with the FIGURE, which is a functional block diagram of a system according to a preferred embodiment of the present invention.

DETAILED DESCRIPTION

With reference now to the FIGURE, there is depicted a functional block diagram of a computer based system 10 for associating defect information with design information. The system 10 is preferably implemented as a software routine on a standard computer platform, such as a personal computer. Most preferably, the system 10 is connected to other systems, such as with a computer network interface, and can thus access information as required from databases that reside in and are maintained on other systems. Thus, the system 10 preferably includes memory, processing capability, data storage, and display capabilities of the type that are customarily provided with computer systems.

The system 10 includes an input 12 for receiving the design information in regard to the integrated circuits. The design information is preferably that which is used in the fabrication of the integrated circuits, such as to produce the masks and reticles used in the photolithographic processing of the integrated circuits. Thus, the design information contains location information, and other information, for the various structures that are used to form the integrated circuits. Most preferably, the design information is contained in the actual design files produced by the integrated circuit designers. However, in other embodiments the design information is adapted from such files, and from other design data such as layer thicknesses, dopant profiles, and so forth.

In some embodiments the input 12 receives the design information manually, such as by way of a keyboard. The design information could also be read in, such as from a floppy disk. However, in more preferred embodiments, the input 12 is used to access the design information across a network from another system on which the design information files are stored.

The system 10 also includes an input 14 for receiving the defect information in regard to the substrate on which the integrated circuits are formed. The defect information is preferably generated by optical inspections of the substrate during the fabrication process, and is most preferably contained in a defect wafer map data structure. By this it is meant that the data structure which includes the defect information also includes location information, such that all of the defects listed in the defect information are also associated with location data, such that the location of each defect on the substrate is known. The inspections can be of one or more of a variety of different types, such as, without limitation, optical, scanning electron microscope, and voltage contrast. It is appreciated that these inspection types are listed in a representative manner only, and that other types of inspections are also comprehended herein.

In some embodiments the input 14 receives the defect information manually, such as by use of a keyboard. The defection information could also be read in, such as from a floppy disk. However, in more preferred embodiments, the input 14 is used to access the defect information across a network from another system on which the defect information files are stored. In a most preferred embodiment, the input 12 and the input 14 are the same input, such as a network interface adapter.

The design information and the defect information is preferably compared by a comparator 16. The comparator 16, which in one embodiment is a software routine running on a personal computer, matches the location information for the design information with the location information for the defect information. The comparator 16 also determines if there is a structure at a given location, and if there is a defect at the same given location. This process can work either from the design information to the defect information, or from the defect information to the design information.

For example, when working from the design information to the defect information, a first location is selected, and the design information is interrogated to determine what structures, if any, are present in that location. Alternately, the design information can be interrogated to determine what structures, if any, are present within a given distance of the first location. Then, the defect information is interrogated to determine what defects, if any, are present in that same location. Alternately, the defect information can be interrogated to determine what defects, if any, are present within a given distance of the first location. This process preferably continues until all locations have been looked at.

Alternately, when working from the defect information to the design information, a first location is selected, and the defect information is interrogated to determine what defects, if any, are present in that location. Alternately, the defect information can be interrogated to determine what defects, if any, are present within a given distance of the first location. Then, the design information is interrogated to determine what structures, if any, are present in that same location. Alternately, the design information can be interrogated to determine what structures, if any, are present within a given distance of the first location. This process preferably continues until all locations have been looked at.

Alternately, rather than interrogating either of the design information or the defect information with a location, one or the other of the databases can be searched until a first entry is found, the associated location for that entry can be determined, and then the other database can be searched to determine whether it contains anything at that location, or within a given distance from that location.

For example, the defect information can be searched for the first entry of a defect, and then the location of that defect is determined. The location information of the first defect is then used to enter the design information database, to see whether a structure exists at that location, or within a given distance of that location. These steps are then preferably repeated until all of the entries in the defect information have been compared to the design information.

Alternately, the design information can be searched for the first entry of a structure, and then the location of that structure is determined. The location information of the first structure is then used to enter the defect information database, to see whether a defect exists at that location, or within a given distance of that location. These steps are then preferably repeated until all of the entries in the design information have been compared to the defect information.

Once the defect information has been compared to the design information, the matching entries from each database are associated with each other by an associator 18, which in the preferred embodiment is a software routing running on the computer based system 10. The associator 18 can selectively determine associations between the defect information and the design information based upon a number of different criteria, as desired. For example, the associator 18 can provide associations for all structures that fall within a given structural classification, such as for all vias having a diameter below a certain value, or all metal lines having a certain width, or all junctions having a given dopant concentration, or all bonding pads disposed within a certain distance of each other, and so forth.

Alternately, the associator 18 can selectively determine associations between the defect information and the design for all defects that fall within a given defect classification, such as bridging metal lines, cracked dielectric, over etched vias, broken traces, and so forth. Thus, the information can be associated in regard to classification criteria based on either the defect information or the design information, or both. In addition, the maximum allowable distance between a structure and a defect for which an association is established can be input or determined by the associator 18.

Thus, it is appreciated it is possible in various embodiments for the output of the associator 18 to be the input for the comparator 16, and in other embodiments for the output of the comparator 16 to be the input for the associator 18. In other embodiments the comparator 16 and the associator 18 work in an interactive, interactive manner, rather than in a one pass serialized manner.

The associations between the design information and the defect information thus derived by the system 10 are a type of yield enhancement data that has not been identified, created, or utilized in the past. This yield enhancement data provides insight as to whether there are structures, or classes of structures, than tend to be more predominantly associated with defects, or classes of defects, and if so, what type of defects those classes of structures are associated with. Such information can be used, for example, in a feedback mode to the design process, to modify the structures so as to reduce the rate of occurrence of such defects.

For example, such information may make it clear that a given structural design is more prone to metal bridging, and a given line is more prone to microtunnelling. These structures can then be redesigned to reduce, and preferably eliminate, the frequency of occurrence of such defects. Thus, in a most preferred embodiment, the system 10 includes a revisor 20 which outputs proposed revisions to the design information, such that integrated circuits that are fabricated in the future, according to the revised design information, have a reduced occurrence of the defects.

The method presented here preferably associates defects to specific design features such as but not limited to via arrays, small metal posts, wide metal bus lines, two metal lines with corners at forty-five degrees from each other, and so forth, which in other words are specific classes of structures found in an integrated circuit design. An algorithm teaches the design features to the system. The algorithm preferably classifies the design features into groups, and then maps the classification locations to the defect data produced by inspections of the integrated circuits that are conducted during the fabrication process. Defects on or near the structures with the design classes can be identified and reported. No electrical testing is done, just a spatial correlation between the defect location in the integrated circuit and the surrounding structural features as described in the design file for the integrated circuit.

Similarly, the inverse could be done, such as by taking all the defect locations found by the inspections conducted during the fabrication process, and using an algorithm that inspects the design file for similar structural features that are in the same location as, or within a given proximal distance to the defects. The result is a distribution of design elements, such as classes of integrated circuit structures, and the defects that occur either at or proximate to those design elements.

This method identifies systematic processing defect types that occur due to interactions between processing and design features. Yield learning on new process technologies could be significantly accelerated by identifying and eliminating these defects early in the process development. Current methods rely on human recognition and understanding of design/process related defects. This method can also be utilized on mature process technologies to identify similar issues.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for producing yield enhancement data for integrated circuits on a substrate, the method comprising steps of:
    comparing a database of physical defects on the substrate to a database of design information for the integrated circuits, and
    associating the physical defects on the substrate with classes of design information by location on the substrate of both the physical defects and elements of the design information to produce the yield enhancement data.

2. The method of claim 1, wherein the database of physical defects comprises a physical defect wafer map.

3. The method of claim 1, wherein the physical defects on the substrate are optically observable physical defects.

4. The method of claim 1, wherein the design information includes structures formed in the integrated circuits.

5. The method of claim 1, wherein the classes of design information comprises classes of physical structures.

6. The method of claim 1, further comprising a step of creating the database of physical defects by inspections of the substrate, where the inspections are conducted at multiple times during fabrication of the integrated circuits.

7. The method of claim 1, further comprising a step of creating the database of design information from design files for the integrated circuits.

8. The method of claim 1, further comprising a step of revising the design information based at least in part on the yield enhancement data.

9. A method for producing yield enhancement data from integrated circuits on a substrate, the method comprising steps of:
   creating a database of design information for the integrated circuits, which design information is used as a template for fabricating the integrated circuits, where the design information includes structure location information for physical structures used to form the integrated circuits,
   binning the physical structures in the design information in the database of design information as belonging to at least one of a number of different classes of physical structures,
   creating a database of physical defects on the substrate during inspections of the substrate that are conducted during processing of the integrated circuits, where the physical defects listed in the database of physical defects are associated with physical defect location information,
   comparing the database of design information with the database of physical defects to create associations between the design information and the physical defects based on matching the structure location information with the physical defect location information, and
   reporting the physical defects based on the classes of the design information with which they are associated as a result of the comparison, to produce the yield enhancement data.

10. The method of claim 9, wherein the database of physical defects comprises a physical defect wafer map.

11. The method of claim 9, wherein the physical defects on the substrate are optically observable physical defects.

12. The method of claim 9, farther comprising a step of revising the design information based at least in part on the yield enhancement data.

13. A computerized system for analyzing physical defects, the computerized system comprising:
   means for receiving design information for integrated circuits, where the integrated circuits are fabricated on a substrate based on the design information, where the design information includes structure location information for physical structures used to form the integrated circuits,
   means for binning the physical structures in the design information in a database of design information as belonging to at least one of a number of different classes of physical structures,
   means for receiving physical defect information for integrated circuits, where the physical defect information contains locations of physical defects on the substrate,
   means for comparing the design information with the physical defect information based on matching the structure location information with the locations of physical defects on the substrate, and
   means for associating the physical defects with the classes of the design information based on physical proximity on the substrate to produce yield enhancement data.

14. The computerized system of claim 13, wherein the physical defect information comprises a physical defect wafer map.

15. The computerized system of claim 13, further comprising means for revising the design information based at least in part on the yield enhancement data.

* * * * *